United States Patent [19]

Sanchez et al.

[11] Patent Number: 4,977,154

[45] Date of Patent: * Dec. 11, 1990

[54] 5-AMINO AND 5-HYDROXY-6-FLUOROQUINOLONES AS ANTIBACTERIAL AGENTS

[75] Inventors: Joseph P. Sanchez, Canton; Ashok K. Trehan, Ann Arbor, both of Mich.

[73] Assignee: Warner-Lambert Company, Morris Plains, N.J.

[ * ] Notice: The portion of the term of this patent subsequent to May 26, 2004 has been disclaimed.

[21] Appl. No.: 918,568

[22] Filed: Oct. 20, 1986

Related U.S. Application Data

[63] Continuation-in-part of Ser. No. 808,122, Dec. 12, 1985, Pat. No. 4,668,680.

[51] Int. Cl.$^5$ .......................................... A61K 31/495
[52] U.S. Cl. ................................. 514/254; 514/312; 544/363; 546/156
[58] Field of Search ........................ 544/363; 546/156; 514/254, 312

[56] References Cited

U.S. PATENT DOCUMENTS

| 4,604,401 | 8/1986 | Mich ................................. 514/312 |
| 4,795,751 | 1/1989 | Matsumoto et al. ................ 514/254 |

FOREIGN PATENT DOCUMENTS 0221463  5/1987  European Pat. Off. .

*Primary Examiner*—Sam Rosen
*Attorney, Agent, or Firm*—Francis J. Tinney

[57] ABSTRACT

Novel 7-piperazine derivatives of 5-amino- and 5-hydroxy-1-cyclopropyl-1,4-dihydro-4-oxoquinoline-3-carboxylic acids as antibacterial agents are described as well as methods for their manufacture, formulation, and use in treating bacterial infections.

10 Claims, No Drawings

5-AMINO AND 5-HYDROXY-6-FLUOROQUINOLONES AS ANTIBACTERIAL AGENTS

This is a continuation-in-part of U.S. Ser. No. 808,122 filed Dec. 12, 1985 now U.S. Pat. No. 4,668,680.

BACKGROUND OF THE INVENTION

1-Cyclopropyl-6-monofluoro- and 6,8-difluoro-1,4-dihydro-4-oxo-quinoline-3carboxylic acids having a piperazino or an N-methylpiperazino group at the 7-position are known from European Patent Publication No. 78362, German Offenlegungschrift No. 3318145 and Belgian Patent No. 899,399. Similarly the 8-chloro-1-cyclopropyl-6-fluoro-1,4-dihydro-4-oxo-quinoline-3-carboxylic acids with piperazinyl side chains at the 7-position are described in European Patent Publication No. 167,763. The compounds are described as broad spectrum antibacterial agents.

5-Amino-1-ethyl-6,8-difluoro-1,4-dihydro-4-oxo7-[1-piperazinyl]-3-quinolinecarboxylic acid is described in Japanese Patent Publication No. 58:174,367. Copending U.S. application Ser. No. 770,897 of Aug. 30, 1985, describes a group of 5-amino-1-cyclopropyl-6,8-difluoroquinolones as broad spectrum antibacterial agents. The amino substituents at the seven-position are limited to pyrrolidines and spiroamines.

It was thus surprising and unexpected to discover that the heretofore never described 7-piperazine derivatives of 5-amino- and 5-hydroxy -1-cyclopropylquinoline-r naphthyridine-3-carboxylic acids of the present invention have not only good broad spectrum antibacterial activity in general but especially better activity against *Pseudomonas aeruginosa,* an important and hard to kill bacteria in antibiotic therapy.

SUMMARY OF THE INVENTION

Accordingly, the present invention is to a compound of the formula

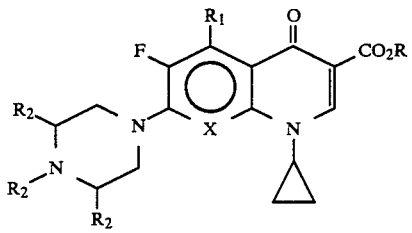

wherein R is hydrogen, a cation or alkyl of one to six carbon atoms; $R_1$ is amino, hydroxy or alkoxy of one to three carbon atoms; X is CH, CBr, CCl, CF, $CCF_3$ or N, and $R_2$ is each independently hydrogen or alkyl of one to six carbon atoms, or a pharmaceutically acceptable acid addition or base salt thereof.

The invention also includes a pharmaceutical composition which comprises an antibacterially effective amount of a compound having structural formula I and the pharmaceutically acceptable salts thereof in combination with a pharmaceutically acceptable carrier.

The invention further includes a method for treating bacterial infections in a mammal which comprises administering an antibacterially effective amount of the above defined pharmaceutical composition to a mammal in need thereof.

DESCRIPTION OF THE PREFERRED EMBODIMENTS

The compounds of the present invention may be readily prepared by reacting a compound of the formula

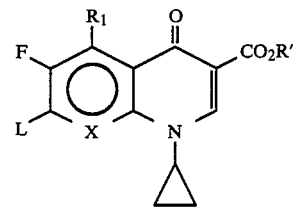

wherein $R_1$ and X are as above defined; R' is hydrogen, alkyl of one to six carbon atoms or benzyl, and L is fluorine or chlorine with a piperazine derivative of the formula

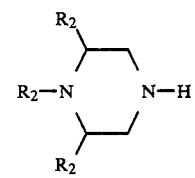

wherein $R_2$ is as above defined, and, when $R_1$ benzyl, converting by known methods the benzyl ester to the free acid, and, if desired, converting by known methods the free acid to a pharmaceutically acceptable acid addition or base salt thereof.

For purposes of this reaction, the piperazines may, if desired, be protected by a group which renders it substantially inert to the reaction conditions. Thus, for example, protecting groups such as the following may be utilized: carboxylic acyl groups such as formyl, acetyl, trifluoroacetyl; alkoxycarbonyl groups such as ethoxycarbonyl, t-butoxycarbonyl, $\beta,\beta,\beta$-trichloroethoxycarbonyl, $\beta$-iodoethoxycarbonyl; aryloxycarbonyl groups such as benzyloxycarbonyl, p-methoxybenzyloxycarbonyl, phenoxycarbonyl; silyl groups such as trimethylsilyl; and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after the reaction between Compound II and the piperazine of formula III, if desired, by procedures known to those skilled in the art. For example, the ethoxycarbonyl group may be removed by acid or base hydrolysis and the trityl group may be removed by hydrogenolysis.

The reaction between the compound of structural formula II and a suitably protected or unprotected piperazine of formula III may be performed with or without a solvent, preferably at elevated temperature, for a sufficient time so that the reaction is substantially complete. The reaction is preferably carried out in the presence of an acid acceptor such as an alkali metal or alkaline earth metal carbonate or bicarbonate, or a tertiary amine such as triethylamine, pyridine, or picoline. Alternatively an excess of the piperazine may be utilized as the acid acceptor.

Convenient solvents for this reaction are nonreactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° to about 150° C.; higher temperatures usually require shorter reaction times.

The removal of the protecting group may be accomplished either before or after isolating the product. Alternatively, the protecting group need not be removed.

The starting compounds having structural formula II are known in the art or, if new, may be prepared from known starting materials by standard procedures or by variations thereof.

Compounds of the formula II may be prepared by a series of reactions starting with 3,4,5,6-tetrafluoroanthranilic acid. The acid is reacted with acetic anhydride and acetic acid to form 2-acetylamino-3,4,5,6-tetrafluorobenzoic acid. This compound is reacted with oxalyl chloride and dichloromethane in the presence of N,N-dimethylformamide catalyst to form 2-acetylamino-3,4,5,6-tetrafluorobenzoyl chloride. This product is treated with n-butyl lithium and malonic half acid ester to form 2-acetylamino-3,4,5,6-tetrafluoro-$\beta$-oxobenzenepropanoic acid ethyl ester.

This product can be converted to 5-acetylamino-1-cyclopropyl-6,7,8-trifluoro-1,4-dihydro-4-oxoquinoline-3-carboxylic acid ethyl ester by a three step reaction. The 2-acetylamino-3,4,5,6-tetrafluoro-$\beta$-oxobenzenepropanoic acid ethyl ester is first treated with triethyl orthoformate and acetic anhydride. After removal of the solvent the residue is treated with a solution of cyclopropylamine in t-butanol. After the reaction is complete a solution of potassium t-butoxide in t-butanol is added. The resulting product is 5-acetylamino-1-cyclopropyl-6,7,8trifluoro-1,4-dihydro-4-oxoquinoline-3-carboxylic acid ethyl ester. The ester is hydrolyzed to form 1-cyclopropyl-5-amino-6,7,8-trifluoro-1,4-dihydro-4-oxo-3-quinolinecarboxylic acid.

An alternate pathway to the compounds of formula II begins with 2-nitro-3,4,5,6-tetrafluorobenzoyl chloride. This starting material is treated with n-butyl lithium and malonic half acid ester to form 2-nitro-3,4,5,6-tetrafluoro-$\beta$-oxobenzenepropanoic acid ethyl ester. This product can be converted to 5-nitro-1-cyclopropyl-6,7,8-trifluoro-1,4-dihydro-4-oxoquinoline-3-carboxylic acid ethyl ester by a three step reaction. The starting material is first treated with triethyl orthoformate and subsequently with cyclopropyl amine in t-butyl alcohol. The product is ring closed with potassium t-butoxide to form 5-nitro-1-cyclopropyl-6,7,8-trifluoro-1,4-dihydro-4-oxoquinoline-3-carboxylic acid ethyl ester. This product is hydrogenated to form the corresponding 5-amino compound. This is then hydrolyzed to form 1-cyclopropyl-5-amino-6,7,8-trifluoro-1,4-dihydro-4-oxo-3-quinolinecarboxylic acid.

The identical procedure is used to synthesize the 5-amino-8-chloro-1-cyclopropyl-6,7-difluoro-1,4-dihydro-4-oxo-3-quinolinecarboxylic acid, the 5-amino-8-bromo-1-cyclopropyl-6,7-difluoro-1,4-dihydro-4-oxo-3-quinolinecarboxylic acid, the 8-chloro-1-cyclopropyl-6,7-difluoro-1,4-dihydro-5-hydroxy-4-oxo-3-quinolinecarboxylic acid, the 8-bromo-1-cyclopropyl-6,7-difluoro-1,4-dihydro-5-hydroxy-4-oxo-3-quinolinecarboxylic acid. In each case the synthesis of these materials begins with the appropriately substituted benzoic acid such as: 2-amino-5-chloro-3,4,6-trifluorobenzoic acid; 2-amino-5-bromo-3,4,6-trifluorobenzoic acid; 5-chloro-3,4,6-trifluoro-2-hydroxybenzoic acid; 5-bromo-3,4,6-trifluoro-2-hydroxybenzoic acid; and 3,4,5,6-tetrafluoro-2-hydroxybenzoic acid. As in the amino examples the hydroxy may be protected by an aryl or alkyl protecting group such as acetyl or methyl. These protecting groups can be removed from the final products by treatment of acid or base for the acetyl and HBr and acetics for the removal of methyl.

The following diagram of reactions, Scheme 1, best illustrates the preparation of compounds of formula II wherein $R_1$ is amino.

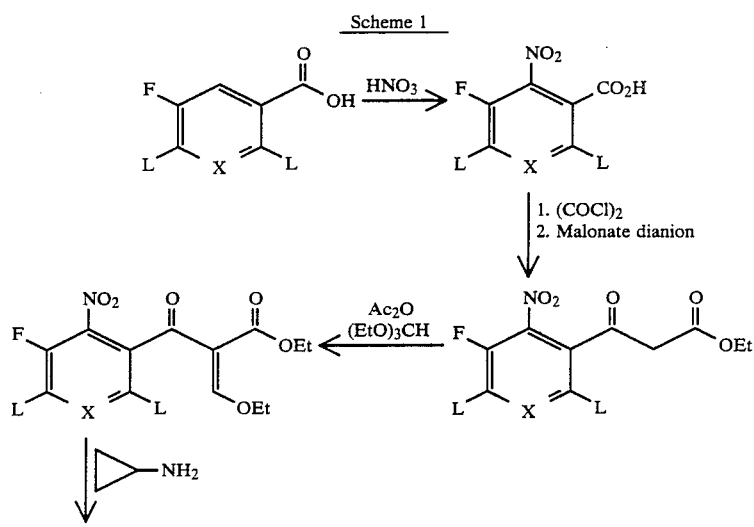

Scheme 1

Scheme 1
-continued

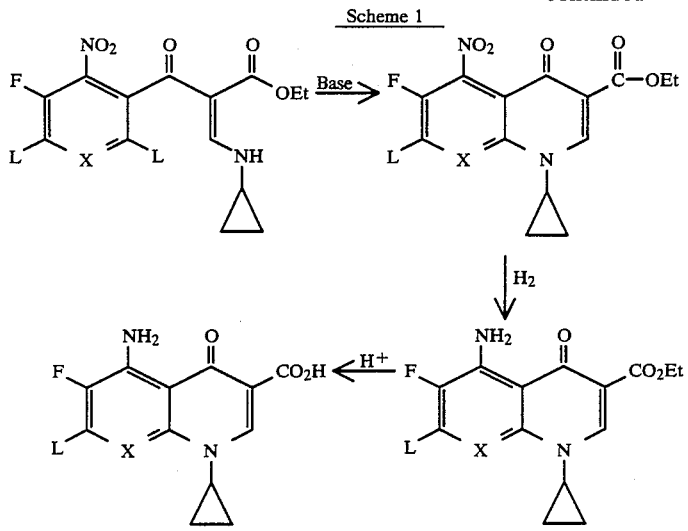

The above compounds, wherein $R_1$ is amino, may be converted to compounds where $R_1$ is hydroxy or alkoxy by first preparing a diazonium salt and subsequent treatment with water or a base, such as an alkoxide to prepare the appropriate alkoxy compound.

Alternatively, compounds of formula II where $R_1$ is hydroxy or alkoxy may be prepared as illustrated by the following diagram, Scheme 2.

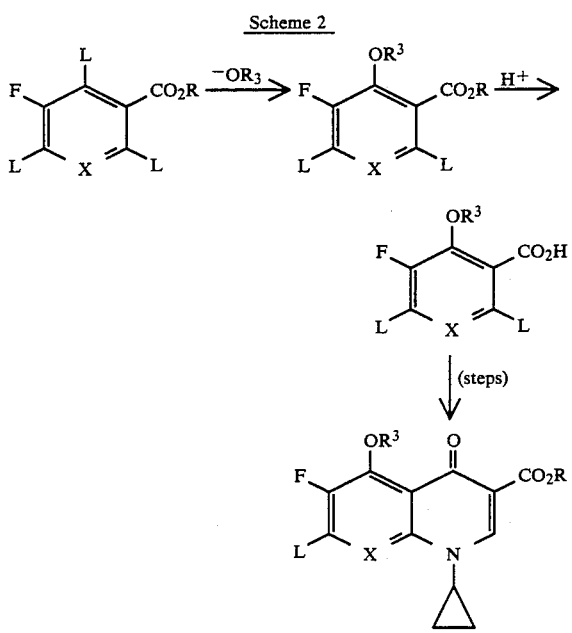

$R_3$ is hydrogen or alkyl of one to three carbon atoms and X, L and R are as previously defined.

The compounds of the invention display antibacterial activity as shown in the following table when tested by the microtitration dilution method as described in Heifetz, et al, Antimicr. Agents & Chemoth., 6, 124 (1974), which is incorporated herein by reference. A comparison of the compounds of the present invention to ciprofloxacin, 1-cyclopropyl-6-fluoro-1,4-dihydro-4-oxo-7-piperazinyl-3-quinolinecarboxylic acid, shows clear superiority of the present compounds especially against Pseudomonas aeruginosa and the gram-positive bacteria.

IN VITRO ANTIBACTERIAL ACTIVITY

| Organisms | Minimal Inhibitory Concentration MIC ($\mu$g/ml) | | |
|---|---|---|---|
| | Compound Ex. 1 | Compound Ex. 2 | Ciprofloxacin |
| *Enterobacter cloacae* MA 2646 | 0.013 | 0.013 | 0.05 |
| *Escherichia coli* Vogel | 0.013 | 0.013 | 0.05 |
| *Klebsiella pneumoniae* MGH-2 | 0.025 | 0.013 | 0.1 |
| *Proteus rettgeri* M 1771 | 0.05 | 0.05 | 0.1 |
| *Pseudomonas aeruginosa* UI-18 | 0.025 | 0.1 | 0.4 |
| *Staphylococcus aureus* H 228 | 0.05 | 0.05 | 3.1 |
| *Streptococcus faecalis* MGH-2 | 0.05 | 0.1 | 0.8 |
| *Streptococcus pneumonia* SV-1 | 0.05 | 0.2 | 1.6 |
| *Streptococcus pyogenes* C-203 | 0.2 | 0.4 | 0.8 |

The compounds of the present invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compounds of the invention can exist in unsolvated as well as solvated forms, including hydrated forms. In general, the solvated forms, including hydrated forms and the like, are equivalent to the unsolvated forms for purposes of the invention.

The alkyl groups contemplated by the invention comprise both straight and branched carbon chains of from one to about six carbon atoms. Representative of such groups are methyl, ethyl, propyl, isopropyl, and the like.

The alkoxy groups contemplated by the invention comprise both straight and branched carbon chains of from one to about three carbon atoms. Representative of such groups are methoxy, ethoxy, propoxy and i-propoxy.

Certain compounds of the invention may exist in optically active forms. The pure D isomer, pure L isomer as well as mixtures thereof, including the racemic mixtures, are contemplated by the invention. Additional asymmetric carbon atoms may be present in a substituent such as an alkyl group. All such isomers as well as mixtures thereof are intended to be included in the invention.

Preferred compounds of the present invention are those of formula I wherein $R_2$ is each independently hydrogen or alkyl of one to three carbon atoms, particularly methyl.

Also preferred are compounds of formula I wherein $R_1$ is amino or hydroxy, and others where X is CCl or CF.

Particularly of value are:

5-amino-1-cyclopropyl-6,8-difluoro-1,4-dihydro-4-oxo-7-(1-piperazinyl)-3-quinolinecarboxylic acid;

5-amino-1-cyclopropyl-6,8-difluoro-1,4-dihydro-7-[4-(methyl)-1-piperazinyl]-4-oxo-3quinolinecarboxylic acid;

5-amino-8-chloro-1-cyclopropyl-6-fluoro-1,4-dihydro4-oxo-7-(1-piperazinyl)-3-quinolinecarboxylic acid;

5-amino-8-chloro-1-cyclopropyl-6-fluoro-1,4-dihydro7-[4-(methyl)-1-piperazinyl]-4-oxo-3-quinolinecarboxylic acid;

5-amino-8-chloro-1-cyclopropyl-6-fluoro-1,4-dihydro-7-[3-(methyl)-1-piperazinyl]-4-oxo-3-quinolinecarboxylic acid, and 8-chloro-1-cyclopropyl-6-fluoro-1,4-dihydro-5-hydroxy-7-[3-(methyl)-1-piperazinyl]-4-oxo-3quinolinecarboxylic acid and pharmaceutically acceptable acid addition or base salts thereof.

The compounds of the invention can be prepared and administered in a wide variety of oral and parenteral dosage forms. It will be obvious to those skilled in the art that the following dosage forms comprise as the active component either a compound of formula I or a corresponding pharmaceutically acceptable salt of a compound of formula I.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

5-Amino-1-cyclopropyl-6,8-difluoro-1,4-dihydro-4-oxo-7-(1-piperazinyl)-3-quinolinecarboxylic acid A suspension of 1.0 g (3.35 mmole) of 5-amino-1-cyclopropyl-6,7,8-trifluoro-1,4-dihydro-4-oxo-3quinolinecarboxylic acid, 1.15 g (13.4 mmole) of piperazine, 1.36 g (13.35 mmole) of triethylamine and 60 ml of acetonitrile is refluxed for three hours and then stirred at room temperature for 16 hours. The precipitate is removed by filtration, washed with acetonitrile and dried in vacuo at 60° C. to give 5-amino-1-cyclopropyl-6,8-difluoro-1,4-dihydro-4-oxo-7-(1-piperazinyl)-3-quinolinecarboxylic acid, mp 257°–259° C.

EXAMPLE 2

5-Amino-1-cyclopropyl-6,8-difluoro-1,4-dihydro-7(4-methyl-1-piperazinyl)-4-oxo-3-quinolinecarboxylic acid A suspension of 1.0 g (3.35 mmole) of 5-amino-1-cyclopropyl-6,7,8-trifluoro-1,4-dihydro-4-oxo-3quinolinecarboxylic acid, 1.36 g (13.35 mmole) of triethylamine and 60 ml of acetonitrile is refluxed for eight hours and stirred at room temperature for 16 hours. The precipitate is removed by filtration, washed with acetonitrile, and dried in vacuo at 45° C. to give 5-amino-1-cyclopropyl-6,8-difluoro-1,4 -dihydro-7-(4-methyl-1-piperazinyl)-4-oxo-3-quinolinecarboxylic acid, mp 247°–248° C.

EXAMPLE 3

5-Amino-8-chloro-1-cyclopropyl-6-fluoro-1,4-dihydro -4-oxo-7-(1-piperazinyl)-3-quinolinecarboxylic acid To 1.57 g (5.00 mmol) of 5-amino-8-chloro-1-cyclopropyl-6,7-difluoro-1,4-dihydro-4-oxo-3quinolinecarboxylic acid in 20 ml of acetonitrile was added 1.7 g (20.0 mmol) of piperazine. The mixture was refluxed for four hours, cooled, filtered, and washed with acetonitrile to give 1.83 g of the title compound.

EXAMPLE 4

1-Cyclopropyl-6,8-difluoro-1,4-dihydro-5-hydroxy-4-oxo-7-[3-(methyl)-1-piperazinyl]-3-ouinolinecarboxylic acid To 1.0 g (3.34 mmol) of the 1-cyclopropyl-6,7,8-trifluoro-1,4-dihydro-5-hydroxy-4-oxo-3-quinolinecarboxylic acid in 20 ml of acetonitrile was added 0.35 g (3.5 mmol) of 3-methylpiperazine. The mixture was refluxed for four hours, cooled, and filtered to give 1.27 g of the title compound.

PREPARATION OF STARTING MATERIALS

EXAMPLE A

3-Chloro-2,4,5-trifluoro-6-nitrobenzoic acid

To a solution of 42.1 g (200 mmol) of 3-chloro-2,4,5-trifluorobenzoic acid (E.P.O. No. 0 183 129) in 100 ml of sulfuric acid was added concentrated nitric acid (50 ml) dropwise such that the reaction temperature stayed below 40° C. The reaction mixture was heated at 60° C. for 18 hours, then poured cautiously onto 500 g of ice water. The aqueous solution was extracted with ether, and the ether extracts were washed with water, dried over magnesium sulfate, and concentrated to give 26.5 g of 3-chloro-2,4,5-trifluoro-6-nitrobenzoic acid.

EXAMPLE B

3-Chloro-2,4,5-trifluoro-6-nitrobenzoyl chloride

To a suspension of 25.6 g (100 mmol) of 3-chloro-2,4,5-trifluoro-6-nitrobenzoic acid in 75 ml of dichloromethane was added 14.0 g (110 mmol) of oxalyl chloride. This mixture was treated with four drops of dry N,N-dimethylformamide, and the rapidly bubbling solution was stirred overnight at room temperature. The mixture was concentrated to give 27.0 g of the title compound which was used without purification in the next step.

EXAMPLE C

Ethyl (3-chloro-2,4,5-trifluoro-6-nitro)-β-oxophenylpropanoate

To 26.4 g (200 mmol) of malonic half ethyl ester in 500 ml of dry tetrahydrofuran at −35° C. was added 91 ml of n-butyllithium (2.2 M, 200 mmol) dropwise. A catalytic amount of bipyridyl (10 mg) was added, and the suspension was warmed to -5° C. Another equivalent of n-butyllithium (91 ml, 200 mmol) was added until the indicator turned pink. The mixture was cooled to −78° C., and a solution of 27 g of 3-chloro-2,4,5-trifluoro-6-nitrobenzoyl chloride in 50 ml of tetrahydrofuran was added dropwise. The reaction mixture was kept at −78° C. for one hour, then warmed to −35° C. and poured into a mixture of ice water (400 ml) and concentrated hydrochloric acid (17 ml). The solution was extracted with dichloromethane; the extracts were combined and washed with 5% sodium bicarbonate, 2 M hydrochloric acid, and water. The dichloromethane was dried over magnesium sulfate and concentrated to give 27.4 g of the title compound.

EXAMPLE D

Ethyl 2-(3-chloro-2,4,5-trifluoro-6-nitrobenzoyl)-3ethoxyacrylate

To 27.4 g (84.1 mmol) of the ethyl (3-chloro-2,4,5-trifluoro-6-nitro)-β-oxophenylpropanoate was added 18.7 g (126 mmol) of triethyl orthoformate and 100 ml of acetic anhydride. The mixture was refluxed for two hours, then cooled to 80° C. and concentrated to give 31.5 g of the title compound.

EXAMPLE E

Ethyl 8-chloro-1-cyclopropyl-6,7-difluoro-1,4-dihydro-5-nitro-4-oxo-3-quinolinecarboxylate The ethyl 2-(3-chloro-2,4,5-trifluoro-6-nitro -benzoyl)-3-ethoxyacrylate prepared in the previous step was dissolved in 200 ml of t-butanol and treated with 5.0 g (88 mmol) of cyclopropylamine. The reaction mixture was warmed to 45° C. and stirred for three hours at that temperature. The solution was then cooled to room temperature and treated with a slurry of 9.4 g (84 mmol) of potassium t-butoxide in 50 ml of t-butanol. The mixture was stirred at 60° C. for five hours; the suspension was filtered, and the solid was washed with water and ether to give 21.7 g of the title compound.

EXAMPLE F

Ethyl 5-amino-8-chloro-1-cyclopropyl-6,7-difluoro-1,4-dihydro-4-oxo-3-quinolinecarboxylate A suspension of 21.7 g (58.2 mmol) of ethyl -chloro-1-cyclopropyl-6,7-difluoro-1,4-dihydro-5-nitro-4-oxo-3-quinolinecarboxylate in 300 ml of ethanol and 300 ml of tetrahydrofuran was catalytically reduced using 3 g of Raney nickel in a hydrogen atmosphere of 50 psi. After twelve hours the mixture was diluted with dichloromethane and the catalyst was removed by filtration. The filtrate was concentrated to give 17.2 g of the title compound.

EXAMPLE G

5-Amino-8-chloro-1-cyclopropyl-6,7-difluoro-1,4-dihydro-4-oxo-3-quinolinecarboxylic acid A suspension of 17.2 g (50.2 mmol) of ethyl 5-amino-8-chloro-1-cyclopropyl-6,7-difluoro-1,4-dihydro-4-oxo-3-quinolinecarboxylate in 100 ml of 6 M hydrochloric acid was refluxed for three hours. The mixture was cooled to room temperature, and the solids were filtered, washed with water and ether, and dried to give 14.2 g of the title compound.

Using the same sequence the following compounds are prepared: 5-amino-8-bromo-1-cyclopropyl-6,7-difluoro-1,4-dihydro-4-oxo-3-quinolinecarboxylic acid; 5-amino-1-cyclopropyl-6,7-difluoro-8-trifluoromethyl-1,4-dihydro-4-oxo-3quinolinecarboxylic acid; 5-amino-1-cyclopropyl-6,7-difluoro-1,4-dihydro-8-methoxy-4-oxo-3quinolinecarboxylic acid; 5-amino-1-cyclopropyl-6,7-difluoro-1,4-dihydro-8-hydroxy-4-oxo-3-quinolinecarboxylic acid; 5,8-diamino-1-cyclopropyl6,7-difluoro-1,4-dihydro-4-oxo-3-quinolinecarboxylic acid, and 5-amino-1-cyclopropyl-6,7-difluoro-1,4-dihydro-4-oxo-3-quinolinecarboxylic acid.

EXAMPLE H

1-Cyclopropyl-6,7,8-trifluoro-1,4-dihydro-5-methoxy4-oxo-3-quinolinecarboxylic acid To 22.4 g (100 mmol) of the 2-methoxy-3,4,5,6-tetrafluorobenzoic acid prepared as in [J. Fluorine Chem., 28 361 (1985)] was added 400 ml of tetrahydrofuran, 1 ml of dimethylformamide, and 13 ml of oxalyl chloride. The acid chloride mixture was concentrated, diluted with 100 ml of tetrahydrofuran, and added to a solution of the dilithio anion of malonic acid monoethylester (200 mmol) in 800 ml of tetrahydrofuran at $-70°$ C. The reaction was stirred for one hour at $-30°$ C., poured over ice and dilute hydrochloric acid and taken into dichloromethane. The product was isolated by an extraction at pH 7, followed by drying the dichloromethane (MgSO$_4$) and concentration. The crude product was then treated neat with 2.5 equivalents of triethylorthoformate and 2.8 equivalents of acetic anhydride at 150° for two hours. The mixture was concentrated and at room temperature a slight excess of cyclopropylamine (6.0 g) was added in 150 ml of t-butanol. The mixture was stirred overnight. To this mixture was added 11.3 g of potassium t-butoxide and the temperature brought to 50° C. The mixture was concentrated after 18 hours and the residue treated with 100 ml of acetic acid and 100 ml of 4N hydrochloric acid. From this mixture after four hours at 100° C., 12.7 g of the title compound precipitated.

In a similar manner, the following compounds were prepared: 8-chloro-1-cyclopropyl-6,7-difluoro-1,4-dihydro-5-methoxy-4-oxo-3-quinolinecarboxylic acid; 8-bromo-1-cyclopropyl-6,7-difluoro-1,4-dihydro-5-methoxy-4-oxo-3-quinolinecarboxylic acid and 1-cyclopropyl-6,7-difluoro-8-trifluoromethyl-1,4-dihydro-5-methoxy-4-oxo-3-quinolinecarboxylic acid.

We claim:

1. A compound of the formula

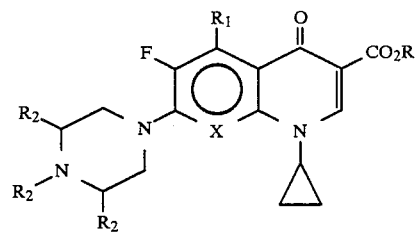

wherein R is hydrogen, a cation or alkyl of one to six carbon atoms; $R_1$ is amino, hydroxy or alkoxy of one to three carbon atoms; X is CH, or CCl; $R_2$ is each independently hydrogen or alkyl of one to six carbon atoms, or a pharmaceutically acceptable acid addition or base salt thereof.

2. A compound as claimed in claim 1, wherein $R_2$ is hydrogen or alkyl of one to three carbon atoms.

3. A compound as claimed in claim 2, wherein $R_1$ is amino or hydroxy.

4. A compound a claimed in claim 3, wherein X is CCl.

5. A compound as claimed in claim 4 and being 5-amino-8-chloro-1-cyclopropyl-6-fluoro-1,4-dihydro-4-oxo-7-(1-piperazinyl)-3-quinolinecarboxylic acid.

6. A compound as claimed in claim 4 and being 5-amino-8-chloro-1-cyclopropyl-6-fluoro-1,4-dihydro-7-[4-(methyl)-1-piperazinyl]-4-oxo-3-quinolinecarboxylic acid.

7. A compound as claimed in claim 4 and being 5-amino-8-chloro-1-cyclopropyl-6-fluoro-1,4-dihydro-7-[3-(methyl)-1-piperazinyl]-4-oxo-3-quinolinecarboxylic acid.

8. A compound as claimed in claim 4 and being 8-chloro-1-cyclopropyl-6-fluoro-1,4-dihydro-5-hydroxy-7-[3-(methyl)-1-piperazinyl]-4-oxo-3-quinolinecarboxylic acid.

9. A pharmaceutical composition comprising an antibacterially effective amount of a compound as claimed in claim 1 together with a pharmaceutically acceptable carrier.

10. A method of treating bacterial infections in mammals which comprises administering to said mammal a pharmaceutical composition as claimed in claim 9 in unit dosage form.

* * * * *